(12) United States Patent
Maignan et al.

(10) Patent No.: US 6,511,670 B1
(45) Date of Patent: Jan. 28, 2003

(54) (POLY)THIAALKYNOIC COMPOUNDS AND PHARMACEUTICAL/COSMETIC COMPOSITIONS COMPRISED THEREOF

(75) Inventors: Jean Maignan, Tremblay (FR); Sylvie Genard, Paris (FR); Serge Michel, Roquefort les Pins (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/548,932

(22) Filed: Apr. 13, 2000

(30) Foreign Application Priority Data

Apr. 15, 1999 (FR) ............................................. 99 04745

(51) Int. Cl.$^7$ ......................... A61K 6/00; A01N 43/76; A01N 43/64; A01N 37/00; A01N 25/00; C07C 231/00; C08H 3/00

(52) U.S. Cl. ....................... 424/401; 514/374; 514/381; 514/506; 514/858; 514/865; 514/886; 514/887; 554/42; 554/44; 554/46; 554/88; 554/101

(58) Field of Search ........................... 424/401; 514/858, 514/865, 886, 887, 506, 381, 374; 554/88, 101, 42, 44, 46

(56) References Cited

U.S. PATENT DOCUMENTS 5,268,494 A * 12/1993 Shroot et al. ................. 554/42

FOREIGN PATENT DOCUMENTS

| EP | 0 342 115 A1 | 11/1989 |
| JP | 49-102616 | 9/1994 |

* cited by examiner

*Primary Examiner*—Michael G. Hartley
*Assistant Examiner*—Michael A. Willis
(74) *Attorney, Agent, or Firm*—Burns, Doane, Swecker & Mathis, L.L.P.

(57) ABSTRACT

Novel pharmaceutically/cosmetically-active (poly) thiaalkynoic compounds have the structural formula (I):

$$R_1\text{—}Y\text{—}CH_2\text{—}C{\equiv}C\text{—}CH_2\text{—}S\text{—}CH_2\text{—}R_2 \quad (I)$$

and are useful for the treatment of a wide variety of disease states, whether human or veterinary, for example inflammation disorders, as well as for the treatment of mammalian skin and hair conditions/disorders.

29 Claims, 5 Drawing Sheets m=1,2,3
2, 4 or 7

(POLY)THIAALKYNOIC COMPOUNDS AND PHARMACEUTICAL/COSMETIC COMPOSITIONS COMPRISED THEREOF

CROSS-REFERENCE TO PRIORITY APPLICATION

This application claims priority under 35 U.S.C. §§119 and or 365 to FR-99/04745 filed in France on Apr. 15, 1999; the entire content of which is hereby incorporated by reference.

BACKGROUND OF THE INVENTION

1. Technical Field of the Invention

The present invention relates to novel (poly)thiaalkynoic compounds and to pharmaceutical/cosmetic compositions comprised thereof; the subject compounds are especially useful in human or veterinary medicine, or alternatively in cosmetic compositions.

The compounds of structural formula (I) below in accordance with the present invention exhibit activity with respect to the transactivation of receptors of the PPAR type and more particularly of receptors of the PPAR-α subtype and find applications, in particular, for the treatment of inflammatory conditions such as rheumatoid arthritis, lupus and psoriasis.

The compounds according to the invention can also be formulated into cosmetic compositions for body and hair hygiene, in particular to regulate the metabolism of cutaneous lipids, to restore the skin barrier function, or to promote differentiation and to inhibit epidermal proliferation.

2. Description of the Prior Art

It is known to this art that a number of substances or active agents play an important role in the inflammatory process in the skin such as acne, dermatoses, such as for example psoriasis, eczema, and the like. These substances, among which are prostaglandins, hydroxyeicosatetraenoic acids, thromboxanes and leukotrienes, all have a common origin which is arachidonic acid (see, in particular, Voorhees, "Leukotrienes and other Lipoxygenase Products in the Pathogenesis and Therapy of Psoriasis and Other Dermathoses," *Arch. Dermatol.*, Vol. 119, Jul. 1983, 541–547).

The formation of these substances results essentially from the conversion, after release, of the arachidonic acid bound by an ester bond to the lipids present in the epidermis (for example the phospholipids).

There have previously been recommended, for the treatment of skin diseases, either cyclooxygenase inhibitors which prevent the formation of prostaglandins, such as indomethacin, vitamin E, and the like; or substances capable of inhibiting lipoxygenases, such as eicosatetraynoic acid.

There have also been proposed, for the treatment of psoriasis, 5,8,11,14-eicosatetraynoic acid, as well as 5,8,11-eicosatriynoic acid and the lower alkyl esters thereof (compare, for example, U.S. Pat. No. 4,190,669), or the replacement of the methylene group at the 3-position in the structure of 5,8,11-eicosatriynoic acid or of 5,8,11,14-eicosatetraynoic acid with a heteroatom, such as sulfur or with a sulfoxide or sulfone group (see, EP-342,115).

SUMMARY OF THE INVENTION

It has now unexpectedly and surprisingly been determined that by shortening the length of the chain of unsaturated fatty acids of the thiaeicosa(poly)ynoic type, compounds were provided which are activators of PPAR-type receptors and, more particularly, activators which are selective for a subtype of PPAR-α receptors.

These acids present, in addition, the advantage of a cost which is much less than their longer-chain homologs.

It has also now been determined, surprisingly, that by replacing the methylene group at the 8-position in the unsaturated 3-thia fatty acid chain with a heteroatom such as sulfur, or with a sulfoxide or sulfone group, activators of PPAR-type receptors and, more particularly, activators which are selective for a subtype of PPAR-α receptors were also provided.

The present invention thus features such novel acids, as well as the derivatives thereof, such as the esters and amides.

The novel compounds according to the invention have the following structural formula (I):

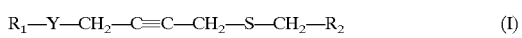

$$R_1—Y—CH_2—C\equiv C—CH_2—S—CH_2—R_2 \qquad (I)$$

in which Y is (a) an —S(O)t radical, wherein t is an integer equal to 0, 1 or 2, (b) a —CH$_2$— radical, (c) a —C≡C— radical, or (d) a —CH=CH— radical; $R_1$ is a linear or branched alkyl radical having from 1 to 18 carbon atoms which is optionally substituted with one or more halogen atoms, a linear or branched alkenyl radical having from 1 to 18 carbon atoms, or a linear or branched alkynyl radical having from 1 to 18 carbon atoms, with the proviso that such $R_1$ radical may comprise one or more oxygen atoms and/or nitrogen atoms and/or sulfur atoms, with the further provisos, that when Y is (b), then $R_1$ contains a number of atoms ranging from 1 to 12, inclusive, preferably from 4 to 12, inclusive, and even more preferably from 6 to 12, inclusive, that when Y is (c), then $R_1$ contains a number of atoms ranging from 1 to 10, inclusive, preferably from 4 to 10, inclusive, and even more preferably from 6 to 10, inclusive, and that when Y is different from (b) and $R_1$ is an unsaturated radical or comprises a heteroatom, then the unsaturation and/or the heteroatom of $R_1$ cannot be at the α position with respect to Y; $R_2$ is (a) a tetrazolyl radical of the formula:

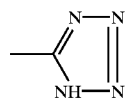

(b) a nitrile radical, (c) an oxazolinyl radical of the formula:

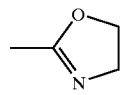

(d) a —CH$_2$OR$_3$ radical, (e) a —CO—R$_4$ radical, wherein $R_3$ and $R_4$ are as defined below; $R_3$ is a hydrogen atom, a lower alkyl radical, a monohydroxyalkyl radical having from 1 to 6 carbon atoms, or a polyhydroxyalkyl radical having from 2 to 6 carbon atoms, a cycloaliphatic radical having from 3 to 6 carbon atoms, or a tetrahydropyranyl radical; $R_4$ is (a) a hydrogen atom, (b) a lower alkyl radical, (c) an —NR' (R") radical, wherein R' and R" are as defined below, or (d) an —OR$_5$ radical, wherein $R_5$ is as defined below; $R_5$ is (a) a hydrogen atom, (b) a linear or branched alkyl radical having from 1 to 18 carbon atoms, (c) a monohydroxyalkyl radical having from 1 to 6 carbon atoms, (d) a polyhydroxyalkyl radical having from 2 to 6 carbon atoms and comprising from 2 to 5 hydroxyl groups, (e) an aryl radical, (f) an aralkyl radical which is optionally substituted with one or more linear or branched alkyl radicals having from 1 to 18 carbon atoms, one or more —CO—R'" radicals, or one or more —O—R'" radicals, wherein R'" is as defined below; R' and R", which may be identical or different, are each a hydrogen atom, a lower alkyl radical, an alkenyl radical having from 3 to 4 carbon atoms, a cycloaliphatic radical having from 3 to 6 carbon atoms, an aryl or aralkyl radical which is optionally substituted, an amino acid or amino sugar residue, with the proviso that R' and R" may together form a heterocycle; and R'" is a hydrogen atom, or a linear or branched alkyl radical having from 1 to 18 carbon atoms.

This invention also relates to and features the salts of the compounds of formula (I) wherein $R_2$ represents a carboxylic acid function, and the geometric and optical isomers of said compounds of formula (I).

When the compounds according to the invention are provided in the form of addition salts with a base, advantageously they are salts of an alkali or alkaline earth metal, or, alternatively, salts of zinc, magnesium or strontium, of an organic amine or the quaternary ammonium salts, when they contain at least one free acid function.

When the compounds of the invention are provided in the form of addition salts with an acid, they are pharmaceutically or cosmetically acceptable salts which are obtained by addition of an inorganic or organic acid, in particular hydrochloric, hydrobromic, sulfuric, acetic, citric, fumaric, hemisuccinic, maleic and mandelic acid.

Figure 1:
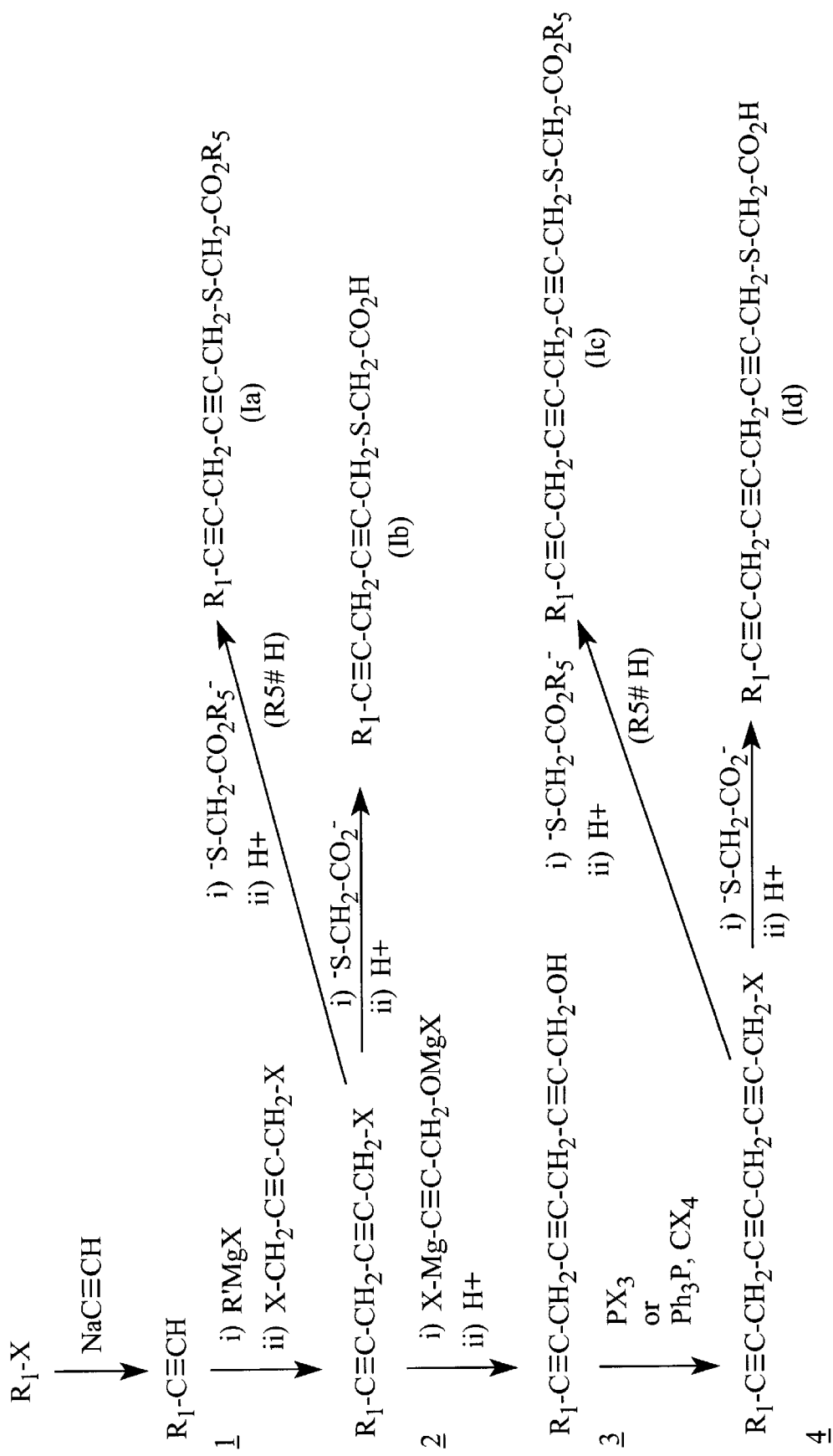
FIG. 1 is an exemplary scheme/mechanism, according to the invention, illustrating the preparation of an anion of an alkyne of formula (1) with a strong base such as an alkyl halomagnesium and then reacting it with an excess of 1,4-dihalo-butyne to form the 1-halo-2,5-diyne derivative (2).

DETAILED DESCRIPTION OF BEST MODE AND SPECIFIC/PREFERRED EMBODIMENTS OF THE INVENTION

More particularly according to the present invention, by "lower alkyl radical" is intended a linear or branched radical having from 1 to 6 carbon atoms and, preferably, the methyl, ethyl, isopropyl, n-butyl, tert-butyl, pentyl or hexyl radicals.

By "alkyl radical" is intended a linear or branched radical having from 1 to 18 carbon atoms which is optionally substituted with one or more halogen atoms. Among the halogen atoms, a fluorine, chlorine or bromine atom is preferred.

The alkyl radicals are preferably selected from among methyl, ethyl, propyl, isopropyl, butyl, tert-butyl, pentyl, hexyl or 2-ethylhexyl, octyl, nonyl, decyl, dodecyl, dodecanyl, tetradecanyl or 3,3,4,4,5,5,6,6,7,7,8,8,8-tridecafluorooctyl radicals.

By "alkenyl radical" is intended a linear or branched radical having from 1 to 18 carbon atoms comprising one or more double bonds and, preferably, the allyl, butenyl, hexenyl, octenyl, decenyl, dodecenyl or tetradecenyl radicals.

By "alkynyl radical" is intended a linear or branched radical having from 1 to 18 carbon atoms comprising one or more triple bonds and, preferably, the propynyl, butyn-2-yl, pentyn-2-yl, hexyn-2-yl, octyn-2-yn, decyn-2-yl or 2-dodecyn-2-yl radicals.

By "monohydroxyalkyl radical" is intended a radical having from 1 to 6 carbon atoms, in particular a 2-hydroxyethyl, 2-hydroxypropyl or 3-hydroxypropyl radical.

By "polyhydroxyalkyl radical" is intended a radical having from 2 to 6 carbon atoms and from 1 to 5 hydroxyl groups, such as the 2,3-dihydroxypropyl, 2,3,4-trihydroxybutyl or 2,3,4,5-tetrahydroxypentyl radicals, or a pentaerythritol residue.

By "cycloaliphatic radical" having from 3 to 6 carbon atoms is preferably intended a cyclopropyl radical, a cyclopentyl radical or a cyclohexyl radical.

By "aryl radical" is intended a phenyl radical, optionally substituted with at least one halogen, lower alkyl, hydroxyl, alkoxy, nitro function, polyether radical, or amino function which is optionally protected with an acetyl group, or which is optionally substituted with at least one lower alkyl radical.

By "aralkyl radical" is intended a benzyl or phenethyl radical which is optionally substituted with at least one halogen, lower alkyl, hydroxyl, alkoxy, nitro function, polyether radical, or amino function which is optionally protected with an acetyl group or which is optionally substituted with at least one lower alkyl radical.

By "amino acid residue" is intended a residue which is derived from one of the 20 amino acids of L or D configuration which constitute mammalian proteins, and preferably a residue which is derived from lysine, glycine or aspartic acid.

By "amino sugar residue" is preferably intended those which are derived from glucosamine, galactosamine, mannosamine or meglumine.

And by "heterocycle" is preferably intended a piperidino, morpholino, pyrrolidino or piperazino radical which is optionally substituted at the 4-position with a $C_1$–$C_6$ alkyl or mono- or polyhydroxyalkyl radical as defined above.

Particulary preferred compounds of formula (I) according to the present invention include:

Methyl 3,8-dithia-11,11,12,12,13,13,14,14,15,15,16,16,16-tridecafluoro-5-hexadecynoate;

3,8-Dithia-11,11,12,12,13113,14,14,15,15,16,16,16-tridecafluoro-5-hexadecynoic acid;

Methyl 3,8-dithia-5-docosynoate;

3,8-Dithia-5-docosynoic acid;
Methyl 3,8-dithia-5-hexadecynoate;
3,8-Dithia-5-hexadecynoic acid;
3-Thia-5-hexadecynoic acid;
Methyl 3,8-dithia-5-heptadecynoate;
3,8-Dithia-5-heptadecynoic acid;
3-Thia-5,8-heptadecadiynoic acid;
3-Thia-5,8-octadecadiynoic acid;
3-Thia-5,8-pentadecadiynoic acid;
3-Thia-5,8,11-octadecatriynoic acid;
3-Thia-5-octadecaynoic acid;
3-Thia-5,8,11-heptadecatriynoic acid;
3-Thia-5-heptadecaynoic acid;
3-Thia-5,8,11-hexadecatriynoic acid;
3-Thia-5,8-hexadecadiynoic acid;
3-Thia-5,8,11-pentadecatriynoic acid;
3-Thia-5-pentadecaynoic acid;
3-Thia-5-tetradecaynoic acid;
3-Thia-5,8,11-heptadecatriynoic acid;

According to the present invention, the compounds of formula (I) which are more particularly preferred are those for which at least one and preferably all of the following conditions are satisfied:

$R_2$ is a —CO—$R_4$ radical;
$R_4$ is a hydroxyl radical;
Y is selected from among:
the radical (c) and $R_1$ is an alkyl radical having from 4 to 10 carbon atoms, or the radical (a) in which t equals 0 and $R_1$ is an alkyl radical having from 4 to 12 carbon atoms, or the radical (b) and $R_1$ is a fluorinated radical having from 4 to 12 carbon atoms.

The present invention also features methods for preparing the compounds of formula (I), in particular according to the reaction schemes shown in FIGS. 1, 2, 3, 4, 5, 6 and 7.

Figure 2:
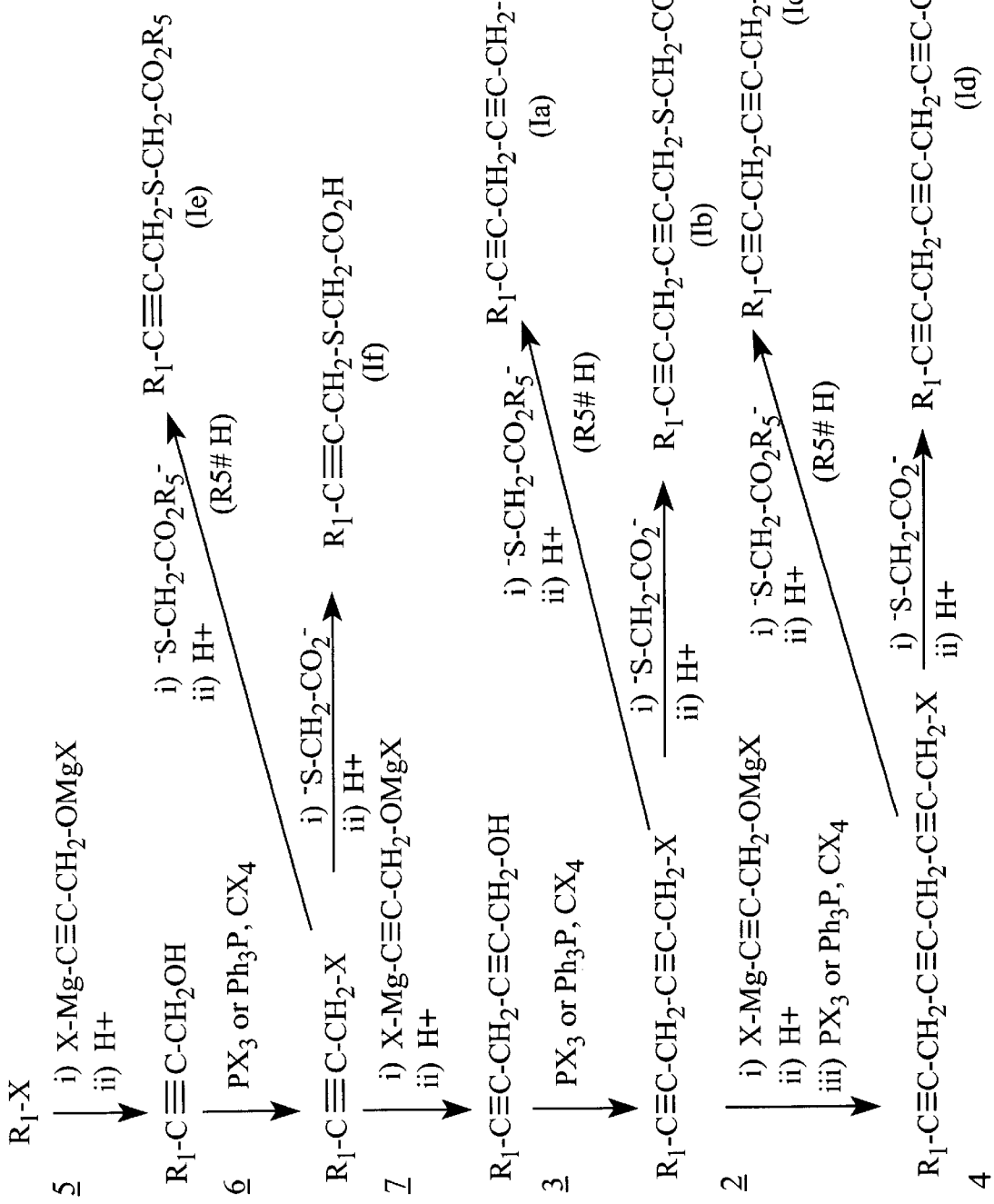
FIG. 2 is an exemplary scheme/mechanism, according to the invention, illustrating the preparation of alkyne intermediates whose triple bond is at the 2-position with respect to the function present at the end of the chain.

Thus, when Y corresponds to a methylene or to a triple bond, the compounds of formula (I) in accordance with this invention may be prepared via one of the two procedures represented in FIGS. 1 and 2.

The first method (FIG. 1) entails preparing the anion of an alkyne of formula (1) with a strong base such as an alkyl halomagnesium and then in reacting it with an excess of 1,4-dihalobutyne to form the 1-halo-2,5-diyne derivative (2). Certain alkynes are commercially available, such as for example 1-heptyne or 1-decyne. The other alkynes of formula $R_1$—C≡C—H are prepared by reacting sodium acetylide with the corresponding halide $R_1$—X.

The 2,5,8-triyne derivatives (4) are prepared by reacting the derivative (2) with the dianion of propargyl alcohol. The triyne alcohol (3) thus obtained is converted to the corresponding halide to provide the 1-halo-2,5,8-triyne derivative having the structure (4).

The alkyne halides (2) or (4) are converted, upon treatment with the dianion of thioglycolic acid or with the thiolate of a mercaptan, into the compounds of the invention of formula (I) in which Y corresponds to a triple bond, $R_1$ being either a saturated alkyl radical or an alkyl radical comprising a site of unsaturation, in particular a triple bond situated at the β position with respect to Y, or, alternatively, a perfluorinated alkyl radical.

The dianion of thioglycolic acid is formed by treating the latter with 2 equivalents of a base. The thiolate of a mercaptan is prepared with one equivalent of a base. This base is an inorganic or organic base, the preferred bases being sodium hydroxide, potassium hydroxide or sodium methoxide.

After reacting the dianion of thioglycolic acid with the alkyne halide, the 3-thiaalkynoic acid of formula (I) is purified by crystallization from an appropriate solvent when it is a solid at room temperature, or by chromatography on silica gel for a compound which is liquid at this temperature. After reacting the anion of an alkyl mercaptan with the alkyne halide, the ester of the 3-thiaalkynoic acid obtained is generally purified by chromatography on a silica column.

The second reaction scheme (FIG. 2) entails directly preparing alkyne intermediates whose triple bond is at the 2-position with respect to the function present at the end of the chain.

The "propyne moiety" is grafted via propargyl alcohol onto an alkyl halide of formula 5 when the alcohol 6 is not commercially available. The alkynyl alcohol 6 is converted to the corresponding halide 7 when 7 is not commercially available. The extension of the chain is obtained by grafting the dianion of propargyl alcohol. The alcohol obtained is then converted to the corresponding halide 2 which may also be obtained according to FIG. 1. This halide 2, when treated with the dianion of propargyl alcohol, provides the alcohol 3 which is in turn converted to a halide 4.

For example, the preparation of 1-halo-2,5-tetradecadiyne is described in French Patent No. 2,584,400.

The dianion of propargyl alcohol is prepared by treating this alcohol with 2 equivalents of a base. The bases used are strong bases such as organolithium compounds, such as, for example, n-butyllithium or organomagnesium compounds such as ethyl or propyl halomagnesium in an anhydrous solvent, preferably an ether such as tetrahydrofuran or diethyl ether. After reaction of this dianion and acidification of the reaction medium, the alkynyl alcohol is purified by distillation or recrystallization. This alcohol is treated in a chlorinated solvent such as dichloromethane or 1,2-dichloroethane, or an ether, with a phosphorus trihalide or a carbon tetrahalide, triphenylphosphine mixture. The alkyne halide thus obtained is purified, depending on its mode of preparation, by distillation (when its stability permits it), or by chromatography.

Figure 3:
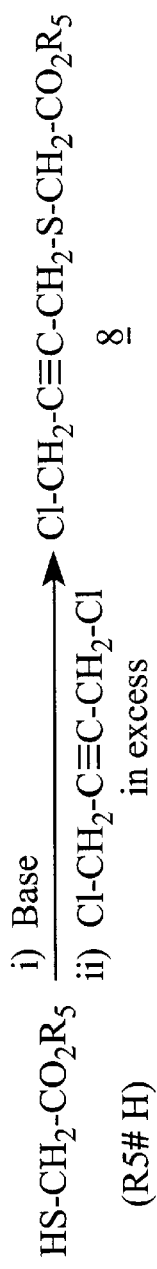
FIG. 3 is an exemplary scheme/mechanism, according to the invention, illustrating the preparation of compounds from an ester 8 obtained by reaction of an anion of alkyl thioglycolate reacted with 1,4-dichlerobutyne used in excess to promote a monosubstitution reaction.
Figure 3:
Figure 4:
FIG. 4 is another exemplary scheme/mechanism, according to the invention, illustrating the preparation of compounds wherein the thiolate R, S— can react on an excess of 1,4-dichloro-2-butyne to form an alkyne that can react with a dianion of thioglycolic acid or the thiolate of a mercaptan to form derivatives of structure (I).

Thus, when Y corresponds to a sulfur atom, the compounds of formula (I) in accordance with the invention may be prepared via one of the two procedures represented in FIGS. 3 and 4.

The first procedure (FIG. 3) entails preparing the compounds of the invention from the ester 8 obtained by reaction of the anion of alkyl thioglycolate such as methyl thioglycolate, which is reacted with 1,4-dichlorobutyne used in excess such as to promote the monosubstitution reaction. The halo ester 8 thus obtained is then reacted with the anions of the mercaptans having the structure $R_1$—SH. These reactions are carried out in the customary dipolar solvents such as alcohols such as methanol or ethers such as tetrahydrofuran.

It should be appreciated that the thiolate $R_1S^-$ can react on an excess of 1,4-dichloro-2-butyne to form the alkyne $R_1$—S—$CH_2$—C≡C—$CH_2$—Cl which can in turn react with the dianion of thioglycolic acid or the thiolate of a mercaptan to form the derivatives having the structure (I) (FIG. 4).

Figure 5:
FIG. 5 is an exemplary scheme/mechanism, according to the invention, illustrating conversion of a derivative of formula (I) to corresponding esters.
Figure 5:
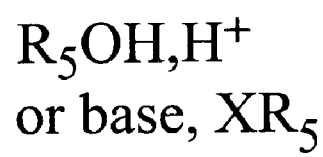
Figure 5:
Figure 5:
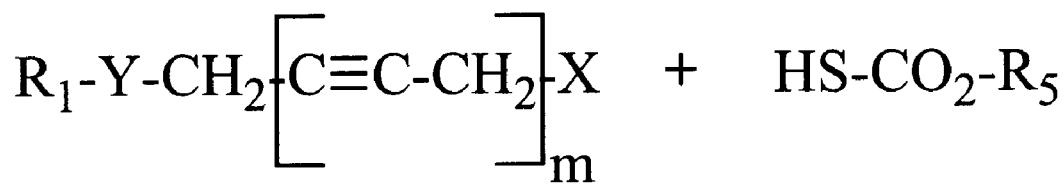
Figure 6:
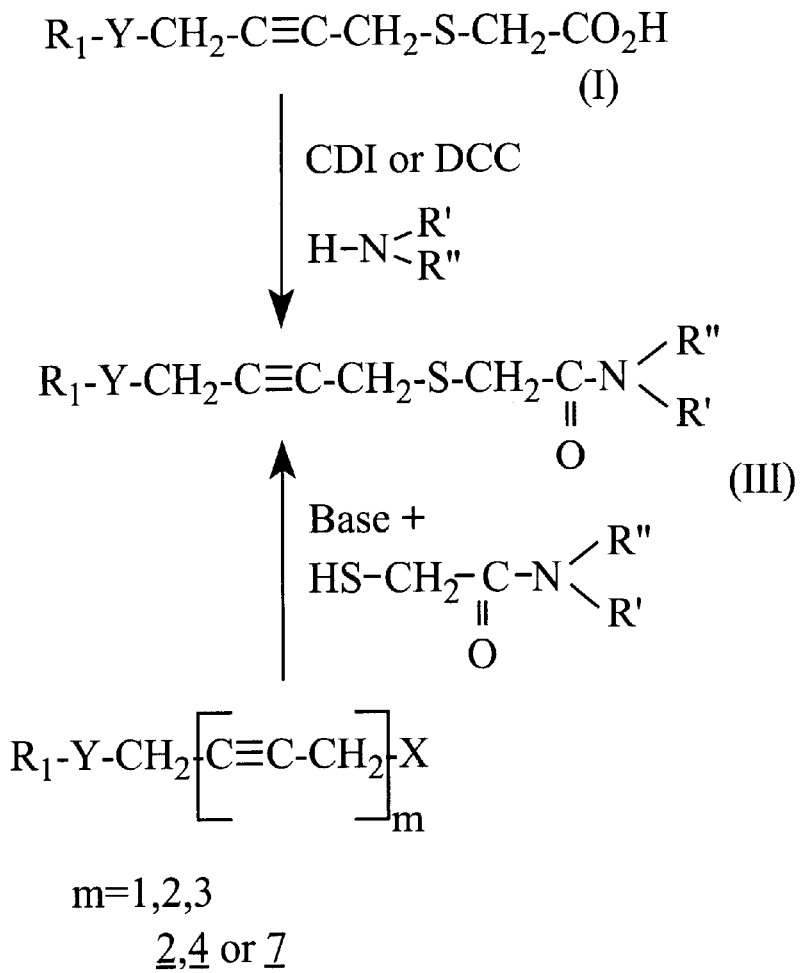
FIG. 6 is an exemplary scheme/mechanism, according to the invention, illustrating preparation of amides within the derivative of formula (I).

The carboxylic acids having the structure (I) may be converted to the corresponding esters according to the customary techniques for converting a carboxylic acid to an ester, namely, by the reaction of an alcohol in an acidic medium or by the reaction for displacing the halogen from an alkyl halide with the sodium or potassium carboxylate function of the acid (I) or, alternatively, by reacting an activated form of the acids of formula (I) with an alcohol $R_5$—OH. By "activated form" is intended the intermediate formed by addition, to an acid solution, of carbonyldiimidazole (CDI), dicyclohexylcarbodiimide (DCC) or any other reagent intended to form an activated form of acid, which is selected from among those known in the literature (FIG. 5).

Another route of preparation is to react the thiolate of an alkyl thioglycolate, treated with 1 equivalent of a base, with a halide of formula 2, 4 or 7.

The amides within the definition of the general formula (I), in which $R_2$ designates the $COR_4$ group and $R_4$ the amino radical —NR' (R") in accordance with the invention, are prepared by reacting an activated form of the acids of formula (I) with an amine in an organic solvent. This activated form of the acid may be either an acid chloride, or an anhydride or, alternatively, the intermediate formed by the addition, to an acid solution, of carbonyldiimidazole (CDI), dicyclohexylcarbodiimide (DCC) or any other reagent intended to form an activated form of an acid, which is selected among from those known in the literature. The latter reaction is preferably carried out in a solvent medium such as dimethylformamide or, alternatively, a chlorinated solvent such as dichloromethane or 1,2-dichloroethane. This reaction is carried out according to the reaction scheme shown in FIG. 6.

Figure 7:
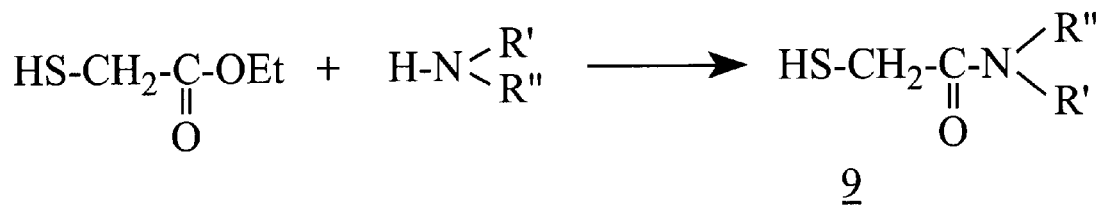
FIG. 7 is an exemplary scheme/mechanism, according to the invention, illustrating the direct preparation of amides without proceeding via the acid of formula (I).

When the thioglycolamides are readily accessible, the amides may be directly prepared without proceeding via this acid of formula (I) by treating the halides 2, 4 or 7 with the thiolate formed beforehand from the thioglycolamide 9. The latter is prepared by the action of an amine H—NR' (R") on ethyl thioglycolate HS—$CH_2$—$CO_2$Et (FIG. 7).

This technique is in fact more simple. The halides 2, 4 or 7, on the one hand, and the potassium or sodium salt of the thioglycolamide 9 on the other, are prepared in methanol or ethanol. The halides 2, 4 or 7 are not purified and their reaction mixture is directly added to a solution of the thioglycolamide salified with 1 equivalent of a base.

The compounds of the invention exhibit properties of activation of the PPAR-type receptors. More particularly, the compounds of the invention exhibit properties of selective activation of the receptors of the PPAR-α subtype.

By "activator of the PPAR-α-type receptors" is intended any compound which exhibits, in a transactivation test, as described in Kliewer et al., Nature, 358, 771–774 (1992), an AC50 relative to PPAR-α of less than or equal to 10 μM. Preferably, the activator of the PPAR-α-type receptors exhibits an AC50 relative to PPAR-α of less than or equal to 3.5 μM and advantageously of less than or equal to 3 μM.

Preferably, the activator of the PPAR-α-type receptors is selective, namely, it exhibits a ratio R1 of AC50 relative to PPAR-α to the AC50 relative to the other subtypes of PPAR (PPAR-δ or PPAR-γ) of less than or equal to $10^{-1}$. Preferably, R1 is less than or equal to 0.05, and more advantageously less than or equal to 0.02.

An AC50 is the concentration of "activator" compound necessary to exhibit 50% of the activity of a reference molecule. This activity is determined with the aid of a reporter enzyme (luciferase) for the activation due to the compound via one of the PPAR receptors, and more particularly of the PPAR-α type.

The activity of the PPAR-type receptors and more particularly of the PPAR-α subtypes has been the subject of many studies. All of the references suggest a role for the PPAR-type receptors in the regulation of the metabolism and the homeostasis of lipids. Exemplary is the publication entitled "Differential Expression of Peroxisome Proliferator-Activated Receptor Subtypes During the Differentiation of Human Keratinocytes", Michel Rivier et al., J. Invest. Dermatol, 111, pp. 1116–1121 (1998), in which a large number of bibliographic references relating to the PPAR-type receptors are listed.

The PPAR-α receptors are involved in the control of inflammation.

The use of the activators of the PPAR-α-type receptors to restore the barrier function, to promote differentiation and to inhibit epidermal proliferation has been described in WO-98/32444.

Furthermore, the use of the activators of the PPAR-α and/or PPAR-γ type receptors to treat skin disorders linked to an abnormality in the differentiation of the epidermal cells has been described in the publication by Michel Rivier et al., J. Invest. Dermatol, 111, pp. 1116–1121 (1998). The skin disorders linked to an abnormality in the differentiation of the epidermal cells are, in particular, psoriasis, eczema, lichen planus, skin lesions associated with a lupus, dermatites such as atopic, seborrhoeic or solar dermatites, keratoses such as seborrhoeic, senile, actinic, photoinduced or follicular keratosis, acne vulgaris, keloids, nevi, verrucas, ichtyoses and skin cancers.

The compounds of formula (I) according to the invention find application in the cosmetic field, in particular in body and hair hygiene and more particularly for regulating the metabolism of cutaneous lipids, for the treatment of skins which are prone to acne, for combating the greasy appearance of the skin or of the hair, or in the treatment of physiologically dry skins.

The use of at least one compound of formula (I) also makes it possible to restore the skin barrier function and/or to promote differentiation and to inhibit epidermal proliferation. Compared with previously known products, these compounds of formula (I) present the advantage of exhibiting, furthermore, other advantageous properties, in particular anti-inflammatory or soothing properties, which renders these compounds less irritant and therefore better tolerated.

The present invention, therefore, also features cosmetic compositions containing, in a cosmetically acceptable carrier, at least one compound of formula (I), one of its optical or geometric isomers or one of its salts, this composition being provided, in particular, in the form of a cream, a milk, an ointment, a lotion, a gel, of lipid or polymeric microspheres or nanospheres or vesicles, of a soap or a shampoo.

The concentration of compound of formula (I) in the subject cosmetic compositions advantageously ranges from 0.0001% to 3% by weight, preferably from 0.001% to 1% by weight, relative to the total weight of the composition.

The present invention also features, as medicaments, the compounds of formula (I) as described above.

The compounds according to the invention are particularly well suited in the following fields of treatment:

(1) dermatological conditions linked to an abnormality in the differentiation of the epidermal cells and in particular psoriasis, eczema, lichen planus, skin lesions associated with a lupus, dermatites such as atopic, seborrhoeic or solar dermatites, keratoses such as seborrhoeic, senile, actinic, photoinduced or follicular keratosis, acne vulgaris, keloids, nevi, verrucas, ichtyoses and skin cancers; (2) inflammatory conditions exhibiting no keratinization disorder, such as arthritis.

This invention also features pharmaceutical compositions containing at least one compound of formula (I) as described above, one of its optical or geometric isomers or one of its salts.

The present invention thus also features pharmaceutical compositions intended, in particular, for the treatment of the abovementioned conditions, and which comprise formulated into a pharmaceutically acceptable carrier, which or diluent therefor, at least one compound of formula (I), one of its optical or geometric isomers, or one of its salts.

The administration of the compositions according to the invention may be carried out by the enteral, parenteral, systemic or topical route. Preferably, the pharmaceutical compositions are packaged in a form appropriate for topical application.

For enteral administration, the compositions, more particularly the pharmaceutical compositions, are advantageously provided in the form of tablets, gelatin capsules, sugar-coated tablets, syrups, suspensions, ointments, solutions, powders, granules, emulsions, lipid or polymeric microspheres or nanospheres or vesicles allowing a controlled release. For parenteral administration, the compositions may be provided in the form of solutions or suspensions for infusion or for injection.

The compounds according to the invention are advantageously administered in a daily dose of about 0.001 mg/kg to 100 mg/kg of body weight in 1 to 3 doses.

For topical administration, the pharmaceutical compositions according to the invention are more particularly intended for the treatment of the skin and of the mucous membranes and may be provided in the form of ointments, creams, milks, pomades, powders, impregnated packs, solutions, gels, sprays, lotions or suspensions. They may also be provided in the form of lipid or polymeric microspheres or nanospheres, or vesicles or of polymeric patches and of hydrogels permitting controlled release. Such compositions for topical administration may be provided either in anhydrous form, or in aqueous form.

The subject compounds are advantageously topically applied a concentration generally ranging from 0.001% to 10% by weight, preferably from 0.01% to 1% by weight, relative to the total weight of the composition.

The compositions described above may of course, in addition, contain inert or even pharmacodynamically active additives and adjunvants, or combinations of these additives and adjuvants, and in particular: wetting agents, depigmenting agents such as hydroquinone, azelaic acid, caffeic acid or kojic acid; emollients; moisturizing agents such as glycerol, PEG 400, thiamorpholinone and derivatives thereof or alternatively urea; antiseborrhoeic or anti-acne agents such as S-carboxylmethylcystein, S-benzylcysteamine, their salts or their derivatives, or benzoyl peroxide; antifungal agents such as ketoconazole or 4,5-polymethylene-3-isothiazolidones; antibacterials, carotenoids and, in particular, β-carotene; antipsoriatic agents such as anthraline and its derivatives; 5,8,11,14-eicosatetraynoic and 5,8,11-eicosatriynoic acids, their esters and amides and, lastly, retinoids.

The subject compositions may also contain taste-enhancing agents, preservatives such as para-hydroxybenzoic acid esters, stabilizing agents, moisture-regulating agents, pH-regulating agents, osmotic pressure-modifying agents, emulsifying agents, UV-A and UV-B screening agents, antioxidants such as α-tocopherol, butylated hydroxyanisole or butylated hydroxytoluene.

Those skilled in this art will of course take care to select the possible compound(s) to be added to the subject compositions such that the advantageous properties intrinsically associated with the present invention are not, or are not substantially altered by the addition envisaged.

In order to further illustrate the present invention and the advantages thereof, the following specific examples of production of active compounds of formula (I), as well as various specific formulations based on such compounds, are now given, it being understood that same are intended only as illustrative and in nowise limitative.

In said examples to follow, parts and percentages are given by weight, unless otherwise indicated.

The various compounds of this invention are prepared from halogenated intermediates, the preparation of which is described in Examples 1, 6, 9, 13, 16, 18 and 20.

EXAMPLE 1

Preparation of Methyl 7-Chloro-3-thia-5-heptynoate 4.22 ml of a 30% solution of sodium methoxide in methanol were added dropwise (such that the temperature did not exceed 15° C.) to a solution of 2 ml of methyl thioglycolate in 20 ml of methanol at 10° C., under an inert atmosphere. The mixture was maintained under stirring for 30 min and then added to a solution of 6.1 ml of 1,4-dichloro-2-butyne in 25 ml of methanol, under an inert atmosphere. The mixture was maintained under stirring for 6 hours at room temperature and then the reaction medium was poured over 100 ml of acid water (98 ml of water+2 ml of concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The 1,4-dichloro-2-butyne in excess in the oil thus obtained was removed by distillation under reduced pressure. The oily distillation residue obtained was chromatographed on a silica gel column ($CH_2Cl_2$) providing two grams of methyl 7-chloro-3-thia-5-heptynoate in the form of a pale yellow oil (yield 65%).

$^1$H NMR 200 MHz $CDCl_3$: 3.39 (s, 2H), 3.44 (t, 2H), 3.73 (s, 3H), 4.15 (t, 2H). $^{13}$C NMR 50 MHz $CDCl_3$: 20.16, 30.45, 32.41, 52.42, 78.25, 81.67, 170.28.

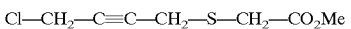

EXAMPLE 2

Preparation of Methyl 3,8-Dithia-11,11,12,12,13,13,14,14,15,15,16,16,16-tridecafluoro-5-hexadecynoate 1.5 ml of a 30% solution of sodium methoxide in methanol was added dropwise to a solution of 3.02 g of Foralkyl EM6 in 30 ml of methanol, under an inert atmosphere. The mixture was maintained under stirring for 30 min and then added to a solution of 1.53 g of methyl 7-chloro-3-thia-5-heptynoate in 10 ml of methanol, under an inert atmosphere. The mixture was maintained under stirring for 12 hours at room temperature and then for 2 hours at 50° C. and then the reaction medium was poured over 100 ml of acid water (98 ml of water+2 ml of concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The oil thus obtained was chromatographed on a silica gel column ($CH_2Cl_2$/heptane 60/40) providing 2.3 grams of methyl 3,8-dithia-11,11,12,12,13,13,14,14,15,15,16,16,16-tridecafluoro-5-hexadecynoate in the form of a pale yellow oil (yield 73.5%).

$^1$H NMR 200 MHz $CDCl_3$: 2.30–2.56 (m, 2H), 2.95–2.86 (m, 2H), 3.34 (t, 2H), 3.39 (s, 2H), 3.43 (t, 2H), 3.74 (s, 3H). $^{13}$C NMR 50 MHz $CDCl_3$: 19.87, 20.29, 22.24, 31.17, 31.61, 32.05, 32.37, 52.34, 78.61, 170.31 (only 1 acetylenic C atom, fluorine-carrying C atoms not out)

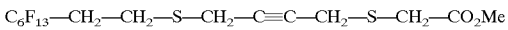

EXAMPLE 3

Preparation of 3,8-Dithia-11,11,12,12,13,13,14,14,15,15,16,16,16-tridecafluoro-5-hexadecynoic Acid The acid was prepared by saponification of the methyl 3,8-dithia-11,11,12,12,13,13,14,14,15,15,16,16,16-tridecafluoro-5-hexadecynoate ester and purified by rapid chromatography on a short silica gel column ($CH_2Cl_2$/MeOH). The acid was thus isolated in the form of a beige wax with a yield of 87%.

$^1$H NMR 200 MHz $CDCl_3$: 2.20–2.60 (m, 2H), 2.85–2.93 (m, 2H), 3.34 (t, 2H), 3.42 (s, 2H), 3.46 (t, 2H).

| Elemental analysis: | C | H | S | F |
|---|---|---|---|---|
| Calculated | 32.19 | 2.12 | 12.28 | 47.28 |
| Found | 32.32 | 2.11 | 12.36 | 47.27 |

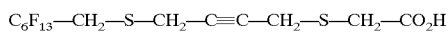

EXAMPLE 4

Preparation of Methyl 3,8-Dithia-5-docosynoate

460 µl of a 30% solution of sodium methoxide in methanol were added to a solution of 665 µl of tetradecanethiol in a 5 ml methanol/2 ml THF mixture, under an inert atmosphere. The mixture was maintained under stirring for 30 min and then 0.47 g of methyl 7-chloro-3-thia-5-heptynoate in 5 ml of methanol was added, under an inert atmosphere. The mixture was maintained under stirring for 8 hours at room temperature and then the reaction medium was poured over 100 ml of acid water (98 ml of water+2 ml concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The wax thus obtained was chromatographed on a silica gel column ($CH_2Cl_2$) providing 1.05 g of methyl 3,8-dithia-5-docosynoate in the form of an oil. (Quantitative yield).

$^1$H NMR 200 MHz $CDCl_3$: 0.88 (S, 3H), 1.15–1.50 (m, 22H), 1.50–1.75 (m, 2H), 2.66 (t, 2H), 2.28 (m, 2H), 3.42 (s, 2H), 3.43–3.47 (m, 4H), 3.75 (s, 3H). $^{13}$C NMR 50 MHz $CDCl_3$: 14.08, 19.71, 20.63, 22.68, 28.87, 29.09, 29.24, 29.34, 29.53, 29.61, 29.67, 31.81, 31.92, 32.55, 52.40, 77.53, 80.08, 170.47.

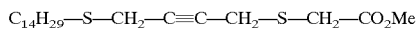

EXAMPLE 5

Preparation of 3,8-Dithia-5-docosynoic Acid

The acid was prepared by saponification of the methyl 3,8-dithia-5-docosynoate ester and purified by recrystallization from boiling heptane. 3,8-dithia-5-docosynoic acid was thus isolated in the form of a white solid with a yield of 81.5%.

$^1$H NMR 200 MHz $CDCl_3$: 0.87 (t, 3H), 1.15–1.46 (m, 22H), 1.46–1.76 (m, 2H), 2.65 (t, 2H), 3.28 (s, 2H), 3.46 (m, 4H). $^{13}$C NMR 50 MHz $CDCl_3$: 14.01, 19.53, 20.55, 22.58, 28.76, 28.92, 29.14, 29.25, 29.44, 29.56, 31.68, 31.81, 32.27, 80.34, 175.73.

| Elemental analysis: | C | H | O | S |
|---|---|---|---|---|
| Calculated | 64.47 | 9.74 | 8.59 | 17.21 |
| Found | 64.09 | 9.64 | 9.24 | 17.06 |

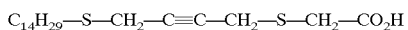

EXAMPLE 6

Preparation of 1-Chloro-5-thia-2-tridecyne 6.46 ml of a 30% solution of sodium methoxide in methanol were added dropwise to a solution of 5 g of octanethiol in 60 ml of methanol, under an inert atmosphere. The mixture was maintained under stirring for 30 min, with stirring, and then added to 9.35 ml of 1,4-dichloro-2-butyne in 70 ml of methanol, under an inert atmosphere. The mixture was maintained under stirring for 12 hours at room temperature and then the reaction medium was poured over 100 ml of acid water (98 ml of water+2 ml concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The 1,4-dichloro-2-butyne in excess in the oil thus obtained was removed by distillation under reduced pressure. The oily distillation residue obtained was chromatographed on a silica gel column ($CH_2Cl_2$) providing 7.5 g of 1-chloro-5-thia-2-tridecyne in the form of a pale yellow oil (yield 94%).

$^1$H NMR 200 MHz $CDCl_3$: 0.82 (s, 3H), 1.1–1.3 (m, 10H), 1.30–1.65 (m, 2H), 2.65 (t, 2H), 3.22 (t, 2H), 4.15 (t, 2H). $^{13}$C NMR 50 MHz $CDCl_3$: 14.21, 19.62, 19.83, 22.77, 28.93, 29.11, 29.30, 30.87, 31.92, 77.45, 83.25.

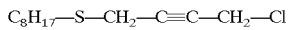

EXAMPLE 7

Preparation of Methyl 3,8-Dithia-5-hexadecynoate 2.03 ml of a 30% solution of sodium methoxide in methanol were added dropwise (such that the temperature did not exceed 15° C.) to a solution of 980 µl of methyl thioglycolate in 10 ml of methanol at 10° C., under an inert atmosphere. The mixture was maintained under stirring for 30 min and then added to a solution of 2.5 g of 1-chloro-5-thia-2-tridecyne in a mixture of 7 ml of methanol with 3 ml of THF under an inert atmosphere. The mixture was maintained under stirring for 15 hours at room temperature and then the reaction medium was poured over 100 ml of acid water (98 ml of water+2 ml concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The oily residue obtained was chromatographed on a silica gel column ($CH_2Cl_2$) providing 2.3 grams of methyl 3,8-dithia-5-hexadecynoate in the form of a pale orange-colored oil (yield 71%).

$^1$H NMR 200 MHz $CDCl_3$: 0.81 (t, 3H), 0.90–1.50 (m, 10H), 1.50–1.61 (m, 2H), 2.62 (t, 2H), 3.25 (t, 2H), 3.39 (s, 2H), 3.41 (t, 2H), 3.72 (s, 3H). $^{13}$C NMR 50 MHz $CDCl_3$: 14.0, 19.53, 20.47, 22.54, 28.75, 28.92, 29.08, 31.61, 31.70, 32.35, 52.35, 77.38, 79.91 170.38

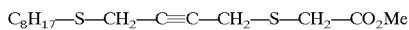

EXAMPLE 8

Preparation of 3,8-Dithia-5-hexadecynoic Acid

The acid was prepared by saponification of the methyl 3,8-dithia-5-hexadecynoate ester and purified by recrystallization from boiling heptane and then from diisopropyl ether. 3,8-dithia-5-hexadecynoic acid was thus isolated in the form of a beige solid with a yield of 67%.

$^1$H NMR 200 MHz CDCl$_3$: 0.84 (t, 3H), 1.1–1.45 (m, 10H), 1.45–1.7 (m, 2H), 2.62 (t, 2H), 3.25 (t, 2H), 3.41 (s, 2H), 3.43 (t, 2H). $^{13}$C NMR 50 MHz CDCl$_3$: 14.09, 19.61, 20.63, 22.64, 28.84, 29.00, 29.17, 31.76, 32.35, 80.55, 176.01.

| Elemental analysis: | C | H | O | S |
|---|---|---|---|---|
| Calculated | 58.29 | 8.39 | 11.09 | 22.23 |
| Found | 58.57 | 8.44 | 11.26 | 21.94 |

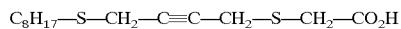

EXAMPLE 9

Preparation of 1-Bromo-2-tridecyne

1-Bromo-2-tridecyne (colorless oil) was prepared from 2-tridecyn-1-ol using the CBr$_4$/triphenylphosphine mixture in dichloromethane to carry out the halogenation. 1-Bromo-2-tridecyne (colorless oil) was thus formed with a yield of 91%.

$^1$H NMR 200 MHz CDCl$_3$: 0.84 (t, 3H), 1.15–1.57 (m, 16H), 2.20 (t.t, 2H), 3.89 (t, 2H).

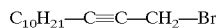

EXAMPLE 10

Preparation of 3-Thia-5-hexadecynoic Acid 2.20 ml of a 30% solution of sodium methoxide in methanol were added dropwise to a solution of 422 µl of thioglycolic acid in 5 ml of methanol, under an inert atmosphere. The mixture was maintained under stirring for 30 min and then added to a solution of 1.5 g of 1-bromo-2-tridecyne in 10 ml of methanol, under an inert atmosphere. The mixture was maintained under stirring for 15 hours at room temperature and then the reaction medium was poured over 100 ml of acid water (98 ml of water+2 ml concentrated H$_2$SO$_4$) and then extracted 3 times with ethyl ether. The combined organic phases were washed 3 times with water and then with a saturated aqueous solution of NaCl before being dried (Na$_2$SO$_4$), filtered and concentrated under vacuum in a rotary evaporator. The oily residue obtained crystallized on cooling. The 3-thia-5-hexadecynoic acid was recrystallized from heptane and then from diisopropyl ether and isolated in the form of white flakes with a yield of 25%.

$^1$H NMR 200 MHz CDCl$_3$: 0.87 (t, 3H), 1.1–1.65 (m, 16H), 2.19 (m, 2H), 3.42 (t, 2H), 3.46 (s, 2H). $^{13}$C NMR 50 MHz CDCl$_3$: 14.11, 18.78, 20.81, 22.68, 28.72, 28.89, 29.12, 29.31, 29.54, 31.90, 32.31, 74.16, 85.04, 175.44.

| Elemental analysis: | C | H | O | S |
|---|---|---|---|---|
| Calculated | 66.62 | 9.69 | 11.83 | 11.86 |
| Found | 66.77 | 9.64 | 12.05 | |

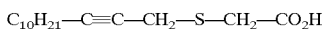

EXAMPLE 11

Preparation of Methyl 3,8-Dithia-5-heptadecynoate 2 ml of a 30% solution of sodium methoxide in methanol were added to a solution of 2 ml of nonanethiol in a 20 ml methanol/5 ml THF mixture, under an inert atmosphere. The mixture was maintained under stirring for 30 min and then added to a solution of 2 g of methyl 7-chloro-3-thia-5-heptynoate in 20 ml of methanol, under an inert atmosphere. The mixture was maintained under stirring for 15 hours at room temperature and then the reaction medium was poured over 100 ml of acid water (98 ml of water+2 ml concentrated H$_2$SO$_4$) and then extracted 3 times with ethyl ether. The combined organic phases were washed 3 times with water and then with a saturated aqueous solution of NaCl before being dried (Na$_2$SO$_4$), filtered and concentrated under vacuum in a rotary evaporator. The oil thus obtained was chromatographed on a silica gel column (CH$_2$Cl$_2$/heptane 85/15) providing 2.1 g of methyl 3,8-dithia-5-heptadecynoate in the form of an orange-colored oil (yield 64%).

$^1$H NMR 200 MHz CDCl$_3$: 0.83 (t, 3H), 1.0–1.65 (m, 14H), 2.64 (t, 2H), 3.26 (t, 2H), 3.39 (s, 2H), 3.42 (t, 2H), 3.73 (s, 3H) $^{13}$C NMR 50 MHz CDCl$_3$: 14.11, 19.64, 20.58, 22.66, 28.85, 29.02, 29.25, 29.48, 31.71, 31.86, 32.46, 52.46, 77.47, 80.02, 170.50.

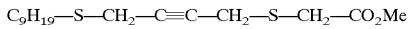

EXAMPLE 12

Preparation of 3,8-Dithia-5-heptadecynoic Acid

The acid was prepared by saponification of the methyl 3,8-dithia-5-heptadecynoate ester and purified by recrystallization from diisopropyl ether. 3,8-dithia-5-heptadecynoic acid was thus isolated in the form of a white solid with a yield of 44%.

$^1$H NMR 200 MHz CDCl$_3$: 0.84 (t, 3H), 1.1–1.45 (m, 12H), 1.45–1.7 (m, 2H), 2.65 (t, 2H), 3.27 (t, 2H), 3.44 (s, 2H), 3.46 (t, 2H). $^{13}$C NMR 50 MHz CDCl$_3$: 14.10, 19.60, 20.62, 22.65, 28.83, 28.99, 29.22, 29.46, 31.74, 31.90, 32.35, 80.41, 176.10.

| Elemental analysis: | C | H | O | S |
|---|---|---|---|---|
| Calculated | 59.56 | 8.66 | 10.58 | 21.20 |
| Found | 59.75 | 8.70 | 10.42 | 20.96 |

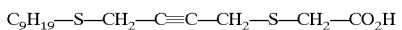

EXAMPLE 13

Preparation of 1-Chloro-2,5-tetradecadiyne 38 ml of a 1M solution of ethyl magnesium bromide in THF were added dropwise, at room temperature, to a solution of 5 grams of 1-decyne in 15 ml of anhydrous THF, under an inert atmosphere. With the addition complete, the mixture was maintained under stirring for 30 min at room temperature and then heated under reflux for 1 h 30 min. The mixture was cooled to room temperature and then 286 mg of copper(I) chloride were added and the mixture was again heated under reflux for 1 hour. It was then cooled to between 40° C. and 50° C. and 12.5 g of 1,4-dichloro-2-butyne dissolved in 25 ml of anhydrous THF were added. The mixture was refluxed for 1 hour and then maintained under stirring for 15 h at room temperature before heating again under reflux for 2 h. The reaction medium was then cooled to 4° C. and hydrolyzed with care with a saturated aqueous solution of $NH_4Cl$. The medium was then extracted 3 times with diethyl ether and the combined organic phases were washed 3 times with water and then with a saturated aqueous solution of NaCl before being dried over $Na_2SO_4$, filtered and concentrated under vacuum in a rotary evaporator. The oily residue containing 1,4-dichloro-2-butyne in excess was purified by distillation under reduced pressure to give 1-chloro-2,5-tetradecadiyne (b.p.=111–114° C., 0.36 mbar) in the form of an orange-colored oil (yield 52.4%).

$^1$H NMR 200 MHz $CDCl_3$: 0.87 (t, 3H), 1.1–1.5 (m, 12H), 2.13 (t.t, 2H), 3.19 (m, 2H), 4.11 (t, 2H). $^{13}$C NMR 50 MHz $CDCl_3$: 9.92, 14.05, 18.62, 22.62, 28.62, 28.84, 29.06, 19.14, 30.68, 31.79, 72.68, 74.87, 81.39, 81.71.

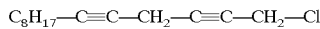

EXAMPLE 14

Preparation of 3-Thia-5,8-heptadecadiynoic Acid 2.02 ml of a 30% solution of sodium methoxide in methanol were added dropwise to a solution of 372 µl of thioglycolic acid in 5 ml of methanol, under an inert atmosphere. The mixture was maintained under stirring for 30 min and then a solution of 1.2 g of 1-chloro-2,5-tetradecadiyne in 6 ml of methanol was added under an inert atmosphere. The mixture was maintained under stirring for 20 hours at room temperature and then the reaction medium was poured over 100 ml of acid water (98 ml of water+2 ml concentrated $H_2SO_4$) and then extracted 3 times with ethyl ether. The combined organic phases were washed 3 times with water and then with a saturated aqueous solution of NaCl before being dried ($Na_2SO_4$) filtered and concentrated under vacuum in a rotary evaporator. The oily residue obtained crystallized on cooling. 3-Thia-5,8-heptadecadiynoic acid was recrystallized from heptane and then from hexane and finally from diisopropyl ether. The acid was thus isolated in the form of beige crystals with a yield of 49.4%.

$^1$H NMR 200 MHz $CDCl_3$: 0.84 (t, 3H), 1.05–1.50 (m, 12H), 2.13 (m, 2H), 3.17 (m, 2H), 3.42 (t, 2H), 3.45 (t, 2H), 9. 75 (broad s, 1H). $^{13}$C NMR 50 MHz $CDCl_3$: 9.88, 14.08, 18.66, 20.53, 22.64, 28.68, 28.88, 29.09, 29.17, 31.82, 32.36, 73.32, 74.62, 79.13, 81.17, 176.21.

| Elemental analysis: | C | H | O | S |
|---|---|---|---|---|
| Calculated | 68.53 | 8.63 | 11.41 | 11.43 |
| Found | 67.88 | 8.59 | 12.02 | 12.21 |

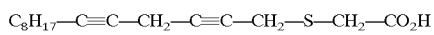

EXAMPLE 15

Preparation of 3-Thia-5,8-heptadecadiyn-1-ol 1.06 ml of a 30% solution of sodium methoxide in methanol were added dropwise, at room temperature, to a solution of 374 µl of 2-mercaptoethanol in 5 ml of anhydrous methanol, under an inert atmosphere. The mixture was maintained under stirring for 30 min and then added to a solution of 1.2 g of 1-chloro-2,5-tetradecadiyne in 6 ml of methanol, under an inert atmosphere. The mixture was maintained under stirring for 15 hours at room temperature and then the reaction medium was poured over 100 ml of acid water (98 ml of water+2 ml concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The oil thus obtained crystallized on cooling. It was purified by recrystallization from a heptane/pentane mixture and then from a heptane/pentane/diisopropyl ether mixture. 3-Thia-5,8-heptadecadiyn-1-ol was thus isolated in the form of pale yellow flakes with a yield of 61%.

$^1$H NMR 200 MHz $CDCl_3$: 0.86 (t, 3H), 1.1–1.6 (m, 12H), 2.12 (m, 2H), 2.89 (t, 2H), 3.15 (m, 2H), 3.26 (t, 2H), 3.78 (t, 2H). $^{13}$C NMR 50 MHz $CDCl_3$: 9.84, 14.06, 18.63, 19.39, 22.61, 28.65, 28.85, 29.06, 29.14, 31.79, 34.84, 60.24, 73.36, 75.86, 78.24, 81.10.

EXAMPLE 16

Preparation of 1-Chloro-2,5-pentadecadiyne 34.5 ml of a 1M solution of ethyl magnesium bromide in THF were added dropwise, at room temperature, to a solution of 5 grams of 1-undecyne in 15 ml of anhydrous THF, under an inert atmosphere with the addition complete, the mixture was maintained under stirring for 30 min at room temperature and then heated under reflux for 1 h 30 min. The mixture was cooled to room temperature and then 260 mg of copper(I) chloride were added and the mixture was again heated under reflux for 1 hour. The mixture was then cooled to room temperature and 11.3 g of 1,4-dichloro-2-butyne were added fairly rapidly. The mixture was refluxed for 1 h 30 min and then maintained under stirring for 15 h at room temperature before heating again under reflux for 3 h. The reaction medium was then cooled to 4° C. and hydrolyzed with care with a saturated aqueous solution of $NH_4Cl$. The medium was then extracted 3 times with diethyl ether and the combined organic phases were washed 3 times with water and then with a saturated aqueous solution of NaCl before being dried over $Na_2SO_4$, filtered and concentrated under vacuum in a rotary evaporator. The oily residue containing 1,4-dichloro-2-butyne in excess was purified by distillation under reduced pressure to give 1-chloro-2,5-pentadecadiyne in the form of a colorless oil with a yield of 37.8%.

$^1$H NMR 200 MHz $CDCl_3$: 0.87 (t, 3H), 1.1–1.55 (m, 14H), 2.14 (m, 2H), 3.19 (m, 2H), 4.13 (t, 2H). $^{13}$C NMR 50 MHz $CDCl_3$: 9.96, 14.10, 18.66, 22.66, 28.64, 28.86, 29.13, 29.27, 29.47, 30.73, 31.86, 72.67, 74.91, 80.86, 81.76.

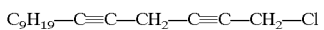

EXAMPLE 17

Preparation of 3-Thia-5,8-octadecadiynoic Acid 3.2 ml of a 300% solution of sodium methoxide in methanol were added dropwise to a solution of 611 µl of thioglycolic acid in 7 ml of methanol, under an inert atmosphere. The mixture was maintained under stirring for 30 min and then a solution of 2 g of 1-chloro-2,5-pentadecadiyne in 20 ml of methanol was added under an inert atmosphere. The mixture was maintained under stirring for 20 hours at room temperature and then the reaction medium was poured over 100 ml of acid water (98 ml of water+2 ml concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The oily residue obtained crystallized on cooling. 3-Thia-5,8-octadecadiynoic acid was recrystallized from diisopropyl ether and thus isolated in the form of a white solid with a yield of 26%.

$^1$H NMR 200 MHz $CDCl_3$ 0.87 (t, 3H), 1.1–1.6 (m, 14H), 2.13 (t.t, 2H), 3.17 (m, 2H), 3.42 (t, 2H), 3.45 (s, 2H), 10.78 (broad s, 1H). $^{13}$C NMR 50 MHz $CDCl_3$: 9.87, 14.10, 18.65, 20.52, 22.66, 28.67, 29.13, 29.26, 29.46, 31.85, 32.35, 73.30, 74.62, 79.11, 81.16, 176.25.

| Elemental analysis: | C | H | O | S |
|---|---|---|---|---|
| Calculated | 69.34 | 8.90 | 10.87 | 10.89 |
| Found | 69.17 | 8.91 | 10.70 | 10.66 |

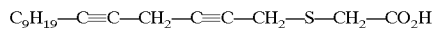

EXAMPLE 18

Preparation of 1-Chloro-2,5-dodecadiyne 38.1 ml of a 1M solution of ethyl magnesium bromide in THF were added dropwise, at room temperature, to a solution of 4 grams of 1-octyne in 15 ml of anhydrous THF, under an inert atmosphere. With the addition complete, the mixture was maintained under stirring for 30 min at room temperature and then heated under reflux for 1 h, 30 min. The mixture was cooled to room temperature and then 287 mg of copper(I) chloride were added and the mixture was again heated under reflux for 1 hour. The mixture was then cooled to room temperature and 9.95 ml of 1,4-dichloro-2-butyne dissolved in 20 ml of anhydrous THF were rapidly added dropwise. The mixture was maintained under stirring for 30 min at room temperature, then it was heated under reflux for 2 h and then maintained under stirring for 15 h at room temperature before being heated under reflux for another 2 h. The reaction medium was then cooled to 4° C. and hydrolyzed with care with a saturated aqueous solution of $NH_4Cl$. The medium was then extracted 3 times with diethyl ether and the combined organic phases were washed 3 times with water and then with a saturated aqueous solution of NaCl before being dried over $Na_2SO_4$, filtered and concentrated under vacuum in a rotary evaporator. The oily residue containing 1,4-dichloro-2-butyne in excess was purified by distillation under reduced pressure and 1-chloro-2,5-dodecadiyne was isolated in the form of a pale yellow oil (yield 36%).

$^1$H NMR 200 MHz $CDCl_3$: 0.88 (t, 3H), 1.1–1.5 (m, 8H), 2.14 (t.t, 2H), 3.20 (m, 2H), 4.13 (t, 2H). $^{13}$C NMR 50 MHz $CDCl_3$: 9.97, 14.04, 18.66, 22.53, 28.53, 28.60, 30.74, 31.31, 72.71, 74.89, 81.46, 81.76.

$C_6H_{13}$—C≡C—$CH_2$—C≡C—$CH_2$—Cl

EXAMPLE 19

Preparation of 3-Thia-5,8-pentadecadiynoic Acid 3.85 ml of a 30% solution of sodium methoxide in methanol were added dropwise to a solution of 742 μl of thioglycolic acid in 8 ml of methanol, under an inert atmosphere. The mixture was maintained under stirring for 30 min and then a solution of 2 g of 1-chloro-2,5-dodecadiyne in 20 ml of methanol was added under an inert atmosphere. The mixture was maintained under stirring for 15 hours at room temperature and then the reaction medium was poured over 100 ml of acid water (98 ml of water+2 ml concentrated $H_2SO_4$) and then extracted 3 times with ethyl ether. The combined organic phases were washed 3 times with water and then with a saturated aqueous solution of NaCl before being dried ($Na_2SO_4$), filtered and concentrated under vacuum in a rotary evaporator. The oily residue obtained crystallized at cold temperature. 3-Thia-5,8-pentadecadiynoic acid was recrystallized from diisopropyl ether.

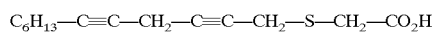

EXAMPLE 20

Preparation of 1-Chloro-2,5-undecadiyne 54.6 ml of a 1M solution of ethyl magnesium bromide in THF were added dropwise, at room temperature, to a solution of 5 grams of 1-heptyne in 15 ml of anhydrous THF, under an inert atmosphere. With the addition complete, the mixture was maintained under stirring for 30 min at room temperature and then heated under reflux for 1 h 30 min. The mixture was cooled to room temperature and then 412 mg of copper(I) chloride were added and the mixture was again heated under reflux for 1 hour. The mixture was then cooled to room temperature and 14.2 ml of 1,4-dichloro-2-butyne were added fairly rapidly. The mixture was refluxed for 1 h, 30 min and then maintained under stirring for 15 h at room temperature before heating again under reflux for 2 h, 30 min. The reaction medium was then cooled to 4° C. and hydrolyzed with care with a saturated aqueous solution of $NH_4Cl$. The medium was then extracted 3 times with diethyl ether and the combined organic phases were washed 3 times with water and then with a saturated aqueous solution of NaCl before being dried over $Na_2SO_4$, filtered and concentrated under vacuum in a rotary evaporator. The oily residue containing 1,4-dichloro-2-butyne in excess was purified by distillation under reduced pressure to give 6.55 g of 1-chloro-2,5-undecadiyne in the form of a pale yellow oil (yield 69%).

$^1$H NMR 200 MHz $CDCl_3$: 0.88 (t, 3H), 1.1–1.5 (m, 6H), 2.13 (t.t, 2H), 3.19 (m, 2H), 4.13 (t, 2H). $^{13}$C NMR 50 MHz $CDCl_3$: 9.92, 13.94, 18.58, 22.17, 28.32, 30.71, 31.02, 72.68, 74.86, 81.38, 81.72.

$C_5H_{11}$—C≡C—$CH_2$—C≡C—$CH_2$—Cl

EXAMPLE 21

Preparation of 3-Thia-5,8,11-heptadecatriynoic Acid

This synthesis was carried out in four stages:

The first stage entailed preparing, from commercially available heptyne, 1-chloro-2,5-undecadiyne by condensation of 1,4-dichlorobutyne (see Example 20).

In the second stage, 2,5,8-tetradecatriynol was obtained by the reaction of the dianion of propargyl alcohol with 1-choro-2,5-undecadiyne.

In the third stage, the 2,5,8-tetradecatriynol was converted to the corresponding bromide by the action of phosphorus tribromide.

Finally, in the fourth stage, this bromide was reacted with the dianion of thioglycolic acid.

(a) Preparation of 2,5,8-Tetradecatriynol

The dianion of propargyl alcohol was prepared by exchanging acidic protons (alcohol and acetylenic) with propylmagnesium chloride. A dilute solution of 4.8 cm³ of propargyl alcohol (0.082 mole) diluted with 10 cm³ of anhydrous THF was added dropwise to a suspension containing 2.1 equivalents of propylmagnesium chloride stirred at 0° under an inert atmosphere in 100 cm³ of THF. This organomagnesium compound (0.17 mole) was prepared by reacting 14 cm³ of chloropropane with 4.2 g of magnesium in THF.

Once the emission of propane had ceased, the temperature was permitted to increase to 20° C. and then the mixture was heated to the boiling temperature of the solvent for 1 h, 30 min. 0.7 g of copper(I) cyanide which was gradually solubilized in the medium was then added. A clear solution was obtained and then, at a temperature of 50° C., 15 g of 1-chloro-2,5-undecadiyne (0.082 mole) diluted with 10 cm³ of THF were added to this dianion and then the mixture was heated, with stirring, for 3 hours at the boiling temperature of the solvent, and then maintained at room temperature overnight.

The reaction mixture was then slowly poured into 200 cm³ of a 1 N aqueous solution of sulfuric acid, and then extracted 3 times with 100 cm³ of ethyl acetate. The organic phases were combined, washed using an ammonium chloride solution, dried over magnesium sulfate and then the ethyl acetate was removed. The crude 2,5,8-tetradecatriynol was dissolved in 150 cm³ of boiling heptane.

The solution was then filtered and then cooled to −20° C. The crystals formed were rapidly drained and dried. 7 g of 2,5,8-tetradecatriynol were thus obtained in the form of beige crystals.

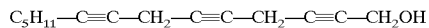

(b) Preparation of 1-Bromo-2,5,8-tetradecatriyne

The alcohol obtained in (a) was directly converted to the corresponding bromide by adding 2 cm³ of phosphorus tribromide (0.0216 mole) to this alcohol diluted in 50 cm³ of ethyl ether. This stirred mixture under an inert atmosphere and protected from light was heated to the boiling temperature of the solvent for 2 hours and then washed at room temperature using a saturated aqueous solution of ammonium chloride.

The organic phase was decanted off and then dried over magnesium sulfate. Three hours later, the magnesium sulfate was removed by filtration. The filtrate containing 1-bromo-2,5,8-tetradecatriyne was used directly in the next stage.

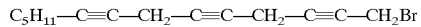

(c) Synthesis of 3-Thia-5,8,11-heptadecatriynoic Acid

A solution containing 0.0346 mole of the dianion of thioglycolic acid was added, with stirring and under an inert atmosphere, to the filtrate thus obtained. This dianion was prepared beforehand by treating, at room temperature and under an inert atmosphere, 2.4 cm³ of thioglycolic acid (0.0346 mole) dissolved in 50 cm³ of methanol with 4.2 g of sodium methoxide (0.076 mole).

One hour after the addition of this dianion to the solution containing 1-bromo-2,5,8-tetradecatriyne, the latter was completely converted.

The reaction mixture was poured into a solution of 350 cm³ of ice-cold 1 N sulphuric acid. The mixture was extracted 3 times with ethyl ether. The ethereal phases were washed with water, dried over sodium sulfate and then concentrated. The crude 3-thia-5,8,11-heptadecatriynoic acid thus obtained in the form of a viscous liquid was dissolved in 100 cm³ of isopropyl ether. Animal charcoal was added to the solution obtained, the mixture was stirred for a quarter of an hour at room temperature and then filtered. The filtrate was concentrated to about 40 cm³ and heptane was added until cloudiness appeared. The mixture was then cooled to −5° C. The crystals formed were rapidly filtered, dried and stored at 0° C. 3 g of 3-thia-2,5,8-heptadecatriynoic acid having a beige color were obtained.

The $^1$H and $^{13}$C NMR spectra were consistent with the structure.

$^1$H NMR 80 MHz CDCl$_3$: 0.80 (t, 3H), 1.1–1.65 (m, 6H), 2.15 (t.t., 2H), 3.16 (s, 4), 3.44 (s, 4H), 10.0–11.0 (unresolved complex, H). $^{13}$C NMR 100 MHz CDCl$_3$: 9.76, 9.95, 14.00, 18.67, 20.52, 22.22, 28.42, 31.08, 32.48, 73.55, 73.75, 75.09, 75.21, 78.33, 81.06, 176.47.

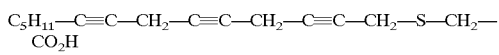

EXAMPLE 22

In this example, various specific formulations based on the compounds according to the invention are illustrated.

(A) ORAL ROUTE:
   (a) 0.2 g tablet:

| | |
|---|---|
| Compound of Example 2 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Oral suspension in 5 ml ampoules:

| | |
|---|---|
| Compound of Example 3 | 0.001 g |
| Glycerine | 0.500 g |
| Sorbitol at 70% | 0.500 g |
| Sodium saccharinate | 0.010 g |
| Methyl para-hydroxybenzoate | 0.040 g |
| Flavoring qs | |
| Purified water qs | 5 ml |

(c) 0.8 g tablet:

| | |
|---|---|
| Compound of Example 5 | 0.500 g |
| Pregelatinized starch | 0.100 g |
| Microcrystalline cellulose | 0.115 g |
| Lactose | 0.075 g |
| Magnesium stearate | 0.010 g |

(d) Oral suspension in 10 ml ampoules:

| | |
|---|---|
| Compound of Example 15 | 0.05 g |
| Glycerine | 1.000 g |
| Sorbitol at 70% | 1.000 g |
| Sodium saccharinate | 0.010 g |
| Methyl para-hydroxybenzoate | 0.080 g |
| Flavoring qs | |
| Purified water qs | 10 ml |

(B) TOPICAL ROUTE:
   (a) Ointment:

| | |
|---|---|
| Compound of Example 10 | 0.020 g |
| Isopropyl myristate | 81.700 g |
| Fluid liquid paraffin | 9.100 g |
| Silica ("Aerosil 200" marked by DEGUSSA) | 9.180 g |

(b) Ointment:

| | |
|---|---|
| Compound of Example 8 | 0.300 g |
| Petroleum jelly | 100 g |

(c) Nonionic water-in-oil cream:

| | |
|---|---|
| Compound of Example 7 | 0.100 g |
| Mixture of emulsifying lanolin alcohols, of waxes and of oils ("anhydrous eucerin" marked by BDF) | 39.900 g |
| Methyl para-hydroxybenzoate | 0.075 g |

|  | Propyl para-hydroxybenzoate | 0.075 g |
|---|---|---|
|  | Sterile demineralized water qs | 100 g |
| (d) | Lotion: |  |
|  | Compound of Example 4 | 0.100 g |
|  | Polyethylene glycol (PEG 400) | 69.900 g |
|  | Ethanol at 95% | 30.000 g |
| (e) | Hydrophobic ointment: |  |
|  | Compound of Example 14 | 0.300 g |
|  | Isopropyl myristate | 36.400 g |
|  | Silicone oil ("Rhodorsil 47 V 300") marketed by RHODIA | 36.400 g |
|  | Beeswax | 13.600 g |
|  | Silicone oil ("Abil 300,000 cst" marketed by GOLDSCHMIDT) | 100 g |
| (f) | Nonionic oil-in-water cream: |  |
|  | Compound of Example 4 | 0.500 g |
|  | Cetyl alcohol | 4.000 g |
|  | Glyceryl monostearate | 2.500 g |
|  | PEG 50 stearate | 2.500 g |
|  | Shea butter | 9.200 g |
|  | Propylene glycol | 2.000 g |
|  | Methyl para-hydroxybenzoate | 0.075 g |
|  | Propyl para-hydroxybenzoate | 0.075 g |
|  | Sterile demineralized water | 100 g |

EXAMPLE 23

A variety of results of biological tests of the compounds of the invention, as well as of comparative examples, are illustrated in this example.

The biological tests carried out corresponded to those described in the application. The technique used to determine the AC50 values was that described in Kliewer et al., *Nature*, 358, 771–774 (1992). Thus, the activating power via PPAR-α, PPAR-γ or PPAR-δ of molecules was evaluated with a transactivation test in which HeLa cells were cotransfected with an expression vector encoding these receptors and a reporter plasmid containing a PPRE response element cloned upstream of a portion of a promoter of the SV40 virus and of the luciferase gene. The cotransfected cells were treated for 24 hours with the molecules to be tested and the activity of the luciferase was determined by luminescence.

Reference 1, reference molecule for the PPAR-α receptors was [4-chloro-6-(2,3-dimethylphenylamino)pyrimidin-2-ylsulfanyl]acetic acid;

Reference 2, reference molecule for the PPAR-δ and PPAR-γ receptors was 5-{4-[2-(methylpyridin-2-ylamino)ethoxy]benzyl}thiazolidine-2,4-dione;

Comparative Examples 1 and 2 were unsaturated fatty acids of the thiaeicosa(poly)ynoic type which were obtained as described in European patent application EP-342,115. Comparative Example 1 was 3-thia-5,8,11,14-eicosatetraynoic acid. Comparative Example 2 was 3-thia-5,8,11-eicosatriynoic acid.

The results obtained in the tests for transactivation of the PPAR-type receptors are reported in the following Table:

TABLE

| Compounds | α | | γ | | δ | |
|---|---|---|---|---|---|---|
|  | Ymax % | AC 50 μM | Ymax % | AC 50 μM | Ymax % | AC 50 μM |
| Reference 1 | 100 | 1.4 | n.a. | n.a. | n.a. | n.a. |
| Reference 2 | n.a. | n.a. | 100 | 0.07 | 100 | 0.13 |
| Example 8 | 91 | 2.9 | n.a. | n.a. | n.a. | n.a. |
| Example 10 | 142 | 1.5 | n.a. | n.a. | n.a. | n.a. |
| Example 14 | 116 | 1 | n.a. | n.a. | n.a. | n.a. |
| Example 21 | 138 | 3 | n.a. | n.a. | n.a. | n.a. |
| Comparative Example 1 | 128 | 4 | 83 | 3 | 125 | 7 |
| Comparative Example 2 | 112 | 5 | 58 | 4 | 74 | 11 | n.a. indicates "not active"

These results evidence the selective activation of the compounds of the invention for the PPAR-α-type receptors.

These results also evidence that unsaturated fatty acids of the thiaeicosa(poly)ynoic type, obtained as described in European patent application EP-342,115, did not exhibit this property of selective activation of the PPAR-α-type receptors.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A (poly)thiaalkynoic compound having the structural formula (I):

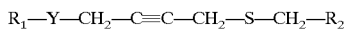

$$R_1-Y-CH_2-C\equiv C-CH_2-S-CH_2-R_2$$

in which Y is (a) an —S(O)t radical, wherein t is an integer equal to 0, 1 or 2, (b) a —CH$_2$— radical, (c) a —C≡C— radical, or (d) a —CH═CH— radical; $R_1$ is a linear or branched alkyl radical having from 1 to 18 carbon atoms which is optionally substituted with one or more halogen atoms, a linear or branched alkenyl radical having from 2 to 18 carbon atoms, or a linear or branched alkynyl radical having from 2 to 8 carbon atoms, with the proviso that such $R_1$ radical may comprise one or more oxygen atoms and/or nitrogen atoms and/or sulfur atoms, with the further provisos, that when Y is (b), then $R_1$ has a number of atoms ranging from 1 and 12, inclusive, that when Y is (c), then $R_1$ has a number of atoms ranging from 1 and 10, inclusive, and that when Y is different from (b) and $R_1$ is an unsaturated radical or comprises a heteroatom, then the unsaturation and/or the heteroatom of $R_1$ cannot be at the a position with respect to Y; $R_2$ is (a) a tetrazolyl radical of formula:

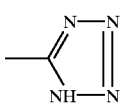

(b) a nitrile radical, (c) an oxazolinyl radical of the formula:

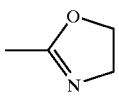

(d) a —CH$_2$OR$_3$ radical, (e) a —CO—R$_4$ radical, wherein $R_3$ and $R_4$ are defined below; $R_3$ is a hydrogen atom, a lower alkyl radical, a monohydroxyalkyl radical having from 1 to 6 carbon atoms, or a polyhydroxyalkyl radical having from 2 to 6 carbon atoms, a cycloaliphatic radical having from 3 to 6 carbon atoms, or a tetrahydropyranyl radical; $R_4$ is (a) a hydrogen atom, (b) a lower alkyl radical, (c) an —NR'(R") radical, wherein R' and R" are as defined below, or (d) an —$OR_5$ radical, wherein $R_5$ is as defined below; $R_5$ is (a) a hydrogen atom, (b) a linear or branched alkyl radical having from 1 to 18 carbon atoms, (c) a monohydroxyalkyl radical having from 1 to 6 carbon atoms, (d) a polyhydroxyalkyl radical having from 2 to 6 carbon atoms and comprising from 2 to 5 hydroxyl groups, (e) an aryl radical, (f) an aralkyl radical which is optionally substituted with one or more linear or branched alkyl radicals having from 1 to 18 carbon atoms, one or more —CO—R''' radicals, or one or more —O—R''' radicals, wherein R''' is as defined below; R' and R", which may be identical or different, are each a hydrogen atom, a lower alkyl radical, an alkenyl radical having from 3 to 4 carbon atoms, a cycloaliphatic radical having from 3 to 6 carbon atoms, an aryl or aralkyl radical which is optionally substituted, an amino acid or amino sugar residue, with the proviso that R' and R" may together form a heterocycle; and R''' is a hydrogen atom, or a linear or branched alkyl radical having from 1 to 18 carbon atoms; and the pharmaceutically/cosmetically acceptable salts, esters, amides and optical and geometric isomers thereof.

2. A (poly)thiaalkynoic compound as defined by claim 1, wherein the acceptable salt is a salt of an alkali or alkaline earth metal, of zinc, of an organic amine, or of an inorganic or organic acid.

3. A (poly)thiaalkynoic compound as defined by claim 1, wherein the lower alkyl radical is selected from the group consisting of methyl, ethyl, isopropyl, n-butyl, tert-butyl, pentyl and hexyl radicals.

4. A (poly)thiaalkynoic compound as defined by claim 1, wherein the linear or branched alkyl radical having from 1 to 18 carbon atoms which is optionally substituted with one or more halogen atoms is selected from the group consisting of methyl, ethyl, propyl, isopropyl, butyl, tert-butyl, pentyl, hexyl, 2-ethylhexyl, octyl, nonyl, decyl, dodecyl, dodecanyl, tetradecanyl and 3,3,4,4,5,5,6,6,7,7,8,8,8-tridecafluorooctyl radicals.

5. A (poly)thiaalkynoic compound as defined by claim 1, wherein the linear or branched alkenyl radical having from 2 to 18 carbon atoms is selected from the group consisting of allyl, butenyl, hexenyl, octenyl, decenyl, dodecenyl and tetradecenyl radicals.

6. A (poly)thiaalkynoic compound as defined by claim 1, wherein the linear or branched alkynyl radical having from 2 to 8 carbon atoms is selected from the group consisting of propynyl, butyn-2-yl, pentyn-2-yl, hexyn-2-yl and octyn-2-yn radicals.

7. A (poly)thiaalkynoic compound as defined by claim 1, wherein the monohydroxyalkyl radical having from 1 to 6 carbon atoms is selected from the group consisting of 2-hydroxyethyl, 2-hydroxypropyl and 3-hydroxypropyl radicals.

8. A (poly)thiaalkynoic compound as defined by claim 1, wherein the polyhydroxyalkyl radical having from 2 to 6 carbon atoms is selected from the group consisting of 2,3-dihydroxypropyl, 2,3,4-trihydroxybutyl, or 2,3,4,5-tetrahydroxypentyl radicals, and the pentaerythritol residue.

9. A (poly)thiaalkynoic compound as defined by claim 1, wherein the aryl radical is a phenyl radical, optionally substituted with at least one halogen, lower alkyl, hydroxyl, alkoxy, nitro function, polyether radical, or amino function which is optionally protected with an acetyl group, or which is optionally substituted with at least one lower alkyl radical.

10. A (poly)thiaalkynoic compound as defined by claim 1, wherein the aralkyl radical is a benzyl or phenethyl radical optionally substituted with at least one halogen, lower alkyl, hydroxyl, alkoxy, nitro function, polyether radical, or amino function which is optionally protected with an acetyl group, or which is optionally substituted with at least one lower alkyl radical.

11. A (poly)thiaalkynoic compound as defined by claim 1, wherein the cycloaliphatic radical having from 3 to 6 carbon atoms is selected from the group consisting of a cyclopropyl radical, a cyclopentyl radical, and a cyclohexyl radical.

12. A (poly)thiaalkynoic compound as defined by claim 1, wherein the amino acid residue is selected from the group consisting of residues derived from lysine, glycine and aspartic acid.

13. A (poly)thiaalkynoic compound as defined by claim 1, wherein the amino sugar residue is selected from the group consisting of residues derived from glucosamine, galactosamine, mannosamine and meglumine.

14. A (poly)thiaalkynoic compound as defined by claim 1, wherein the heterocycle is a heterocyclic radical selected from the group consisting of piperidino, morpholino, pyrrolidino and piperazino radicals optionally substituted at the 4-position with a $C_1$–$C_6$ alkyl radical or with a mono- or polyhydroxyalkyl radical.

15. A (poly)thiaalkynoic compound as defined by claim 1, wherein the compound is methyl 3,8-dithia-11,11,12,12,13,13,14,14,15,15,16, 16,16-tridecafluoro-5-hexadecynoate; 3,8-dithia-11,11,12,12,13,13,14,14,15,15,16,16,16-tridecafluoro-5-hexadecynoic acid; methyl 3,8-dithia-5-docosynoate; 3,8-dithia-5-docosynoic acid; methyl 3,8-dithia-5-hexadecynoate; 3,8-dithia-5-hexadecynoic acid; 3-thia-5-hexadecynoic acid; methyl 3,8-dithia-5-heptadecynoate; 3,8-dithia-5-heptadecynoic acid; 3-thia-5,8-heptadecadiynoic acid; 3-thia-5,8-octadecadiynoic acid; 3-thia-5,8-pentadecadiynoic acid; 3-thia-5-octadecaynoic acid; 3-thia-5,8,11-heptadecatriynoic acid; 3-thia-5-heptadecaynoic acid; 3-thia-5,8,11-hexadecatriynoic acid; 3-thia-5,8-hexadecadiynoic acid; 3-thia-5,8,11-pentadecatriynoic acid; 3-thia-5-pentadecaynoic acid; or 3-thia-5-tetradecaynoic acid.

16. A (poly)thiaalkynoic compound as defined by claim 1, wherein at least one of the following conditions is satisfied:

$R_2$ is a —CO—$R_4$ radical;

$R_4$ is a hydroxyl radical; and

Y is selected from:

the radical (c) and $R_1$ is an alkyl radical having from 4 to 10 carbon atoms, or the radical (a) in which t equals 0 and $R_1$ is an alkyl radical having from 4 to 12 carbon atoms, or the radical (b) and $R_1$ is an alkyl radical substituted with one or more fluorine atoms having from 4 to 12 carbon atoms.

17. A cosmetic composition comprising at least one (poly)thiaalkynoic compound as defined by claim 1, formulated into a cosmetically acceptable vehicle, diluent or carrier therefor.

18. A cosmetic composition as defined by claim 17, comprising from 0.0001% to 3% by weight of said at least one (poly)thiaalkynoic compound.

19. A method for regulating the metabolism of cutaneous lipids, for treating acne-prone skin, for combating the greasy appearance of the skin or of the hair, or for treating physiologically dry skin, comprising administering to a mammalian subject in need of such treatment, an effective amount of at least one (poly)thiaalkynoic compound as defined by claim 1.

20. A method for improving the skin barrier function, or promoting skin differentiation and inhibiting epidermal proliferation, comprising administering to a mammalian subject in need of such treatment, an effective amount of at least one (poly)thiaalkynoic compound as defined by claim 1.

21. A cosmetic composition as defined by claim 17, formulated as a cream, milk, ointment, lotion, gel, lipid or polymeric microspheres, nanospheres or vesicles, soap, or shampoo.

22. A cosmetic composition as defined by claim 17, adapted for topical application.

23. A pharmaceutical composition comprising at least one (poly)thiaalkynoic compound as defined by claim 1, formulated into a pharmaceutically acceptable vehicle, diluent or carrier therefor.

24. A pharmaceutical composition as defined by claim 23, adapted for enteral, parenteral, systemic or topical administration.

25. A method for treating an abnormality in the differentiation of epidermal cells, for treating psoriasis, eczema, lichen planus, lupus-associated skin lesions, atopic, seborrhoeic or solar dermatites, seborrhoeic, senile, actinic, photoinduced or follicular keratosis, acne vulgaris, keloids, nevi, verrucas, ichtyoses, skin cancer, an inflammatory condition exhibiting no keratinization disorder, or arthritis, comprising administering to a mammalian subject in need of such treatment, an effective amount of at least one (poly)thiaalkynoic compound as defined by claim 1.

26. A pharmaceutical composition as defined by claim 23, formulated as tablets, capsules, granules, a syrup, suspension, ointment, solution, powder, emulsion, lipid or polymeric microspheres or nanospheres, or controlled release vesicles.

27. A pharmaceutical composition as defined by claim 23, adapted for topical application.

28. A pharmaceutical composition as defined by claim 23, adapted for infusion or injection.

29. A method for activating the PPAR-type receptors of a mammalian subject in need of such treatment, comprising administering to such mammalian subject, an effective amount of at least one (poly)thiaalkynoic compound as defined by claim 1.

* * * * *